(12) United States Patent
Moon et al.

(10) Patent No.: US 6,492,523 B2
(45) Date of Patent: Dec. 10, 2002

(54) METHOD FOR PREPARING AMLODIPINE

(75) Inventors: Young-Ho Moon, Kyungki-do (KR);
Nam-Du Kim, Kyungki-do (KR);
Kyung-Ik Lee, Incheon (KR);
Kwan-Sun Lee, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 10/095,854

(22) Filed: Mar. 11, 2002

(65) Prior Publication Data

US 2002/0132834 A1 Sep. 19, 2002

(30) Foreign Application Priority Data

Mar. 13, 2001 (KR) .............................................. 01-12858

(51) Int. Cl.$^7$ ............................................. C07D 211/86
(52) U.S. Cl. ....................................................... 546/321
(58) Field of Search ........................................ 546/321

(56) References Cited

U.S. PATENT DOCUMENTS

| 4,515,799 A | * | 5/1985 | Campbell et al. ........... 514/341 |
| 5,389,654 A | * | 2/1995 | Furlon et al. ................. 546/321 |
| 6,046,337 A | * | 4/2000 | Bózsing ...................... 546/321 |

* cited by examiner

Primary Examiner—Patricia L. Morris
(74) Attorney, Agent, or Firm—Anderson Kill & Olick, PC

(57) ABSTRACT

Amlodipine is prepared in a high yield by subjecting a pyrrole derivative, methyl aminocrotonate and 2-chlorobenzaldehyde to a Hantzsch reaction, and converting the pyrrole residue of the resulting 1,4-dihydropyridine derivative to an amine group by the action of hydroxylamine hydrochloride.

5 Claims, No Drawings

METHOD FOR PREPARING AMLODIPINE

FIELD OF THE INVENTION

The present invention relates to a synthetic method of preparing amlodipine in a high yield.

BACKGROUND OF THE INVENTION

Amlodipine, a generic name for the compound of formula (I), 3-ethyl-5-methyl-2-(2-aminoethoxy-methyl)-4-(2-chlorophenyl)-6-methyl- 1,4-dihydro-3,5,-pyridine dicarboxylate, is a long-term calcium-channel blocker useful for treating cadiovacular diseases such as stenocardia, hypertension and congestive cardioplegic. This compound is asymmetric due to the presence, around the rotationally restricted biaryl axis, of two different ester residues:

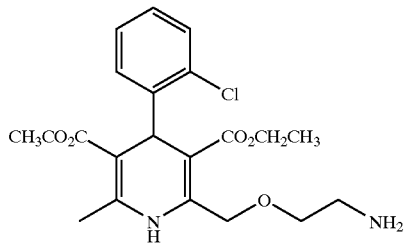

There have been reported a number of methods for amlodipine synthesis but these methods generally suffer from the problem of low productivity caused by low yields observed at the critical Hantzsch reaction step, as further explained below.

For example, Korean Patent Publication No. 87-909 discloses a method for preparing amlodipine represented by Scheme 1: a 1,4-dihydropyridine derivative is obtained by performing a Hantzsch reaction of an azide compound with methyl aminocrotonate and 2-chloro-benzaldehyde, and the azido residue thereof is reduced.

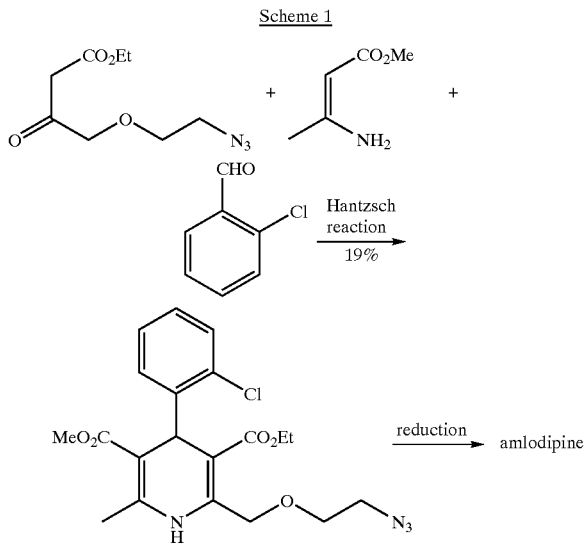

wherein Et and Me represent ethyl and methyl, respectively

However, this method gives a yield of only 19% and is not suitable for a large scale production due to the explosion hazard of the azide compound.

The method disclosed in Korean Patent Publication No. 86-1921 is illustrated as Scheme 2 below, wherein a Hantzsch reaction is conducted by using a derivative having a phthalimide amine protective group, followed by removing the amine protective group to give amlodipine.

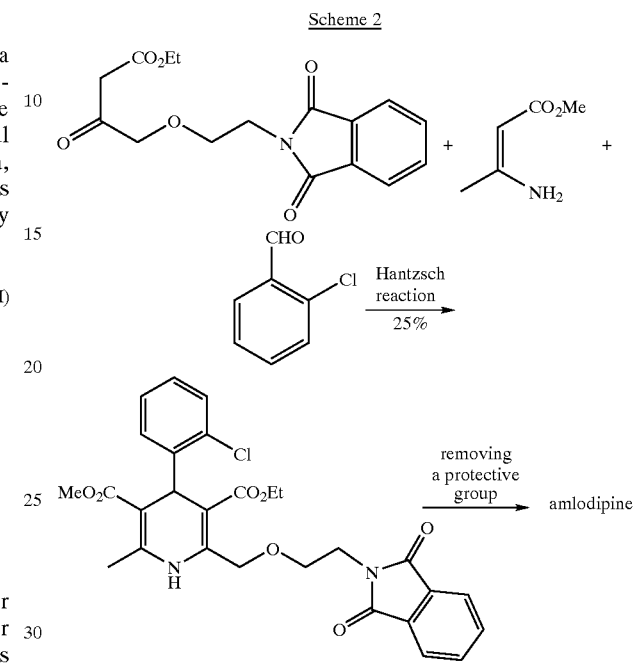

wherein Et and Me represent ethyl and methyl, respectively.

However, this method also has a problem in that the yield of Hantzsch reaction is rather low, e.g., 25%.

Korean Patent Publication No. 87-909 discloses a method for preparing amlodipine described as Scheme 3 below: a Hantzsch reaction is performed using a derivative whose amine group is protected by two benzyl groups, followed by removing the benzyl groups.

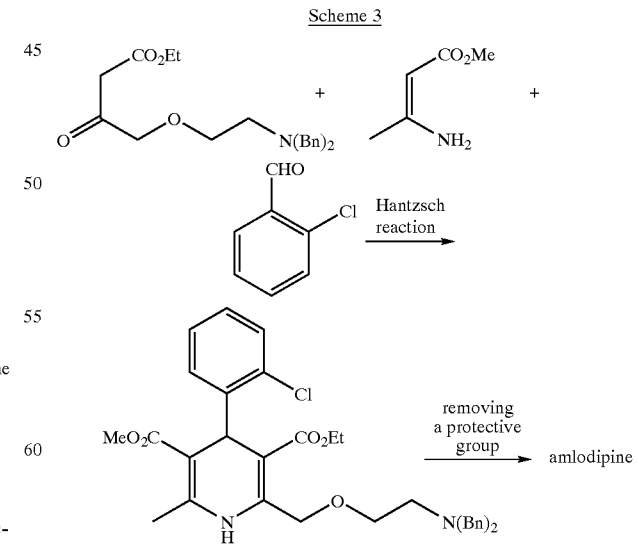

wherein Bn, Et and Me represent benzyl, ethyl and methyl, respectively

This method also entails a low yield of 10%, and has the problem that two-step hydrogenation is required to remove the benzyl groups.

U.S. Pat. No. 5,389,654 describes a method of preparing amlodipine besylate (amlodipine benzenesulphonate) presented as Scheme 4 below, wherein a Hantzsch reaction is carried out using a derivative whose amino group is protected by a triphenylmethyl group, followed by removing the amine protective group by benzene sulfonic acid treatment.

Scheme 4

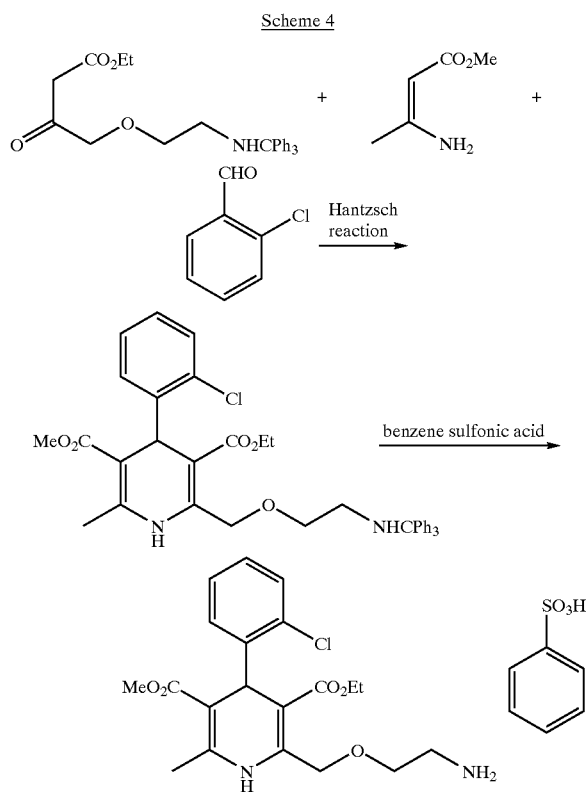

wherein Ph, Et and Me represent phenyl, ethyl and methyl, respectively

Again, this complicated method offers a very low yield of 7%.

According to the method disclosed in U.S. Pat. No. 6,046,337 which is represented as Scheme 5 below, a Hantzsch reaction is performed using a halogenated derivative and the halogen group of the resulting product is subsequently converted into an amine group.

Scheme 5

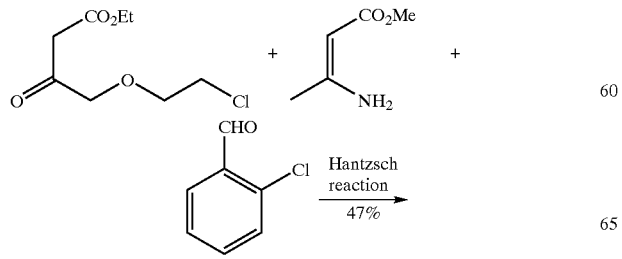

-continued

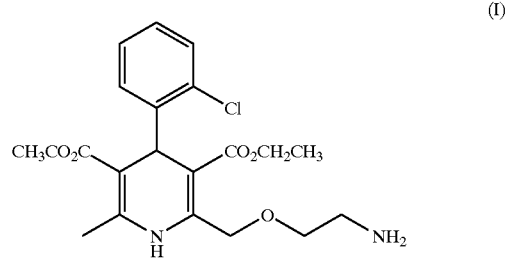

wherein Et and Me represent ethyl and methyl, respectively.

Since the chlorine-containing product is non-reactive in the subsequent amine substitution reation, it must be converted first to the corresponding iodine derivative. Accordingly, regardless of the halogen derivative used, the overall yield of amlodipine is 22% or below.

Accordingly, these prior art methods all suffer from the problem of low yield, calling for an improved method capable of producing amlodipine in a high yield.

SUMMARY OF THE INVENTION

Accordingly, it is a primary object of the present invention to provide an improved method of preparing amlodipine in a high yield.

In accordance with one aspect of the present invention, there is provided a method of preparing amlodipine of formula (I) which comprises:

(a) performing a Hantzsch reaction of a compound of formula (II) with aminocrotonate of formula (III) and 2-chlorobenzaldehyde of formula (IV) to obtain a compound of formula (V); and (b) treating the compound of formula (V) with hydroxylamine hydrochloride in a mixture of water and an organic solvent:

(I)

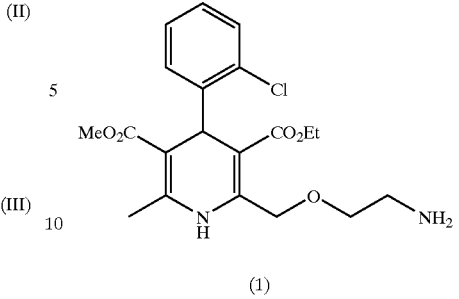

(II)

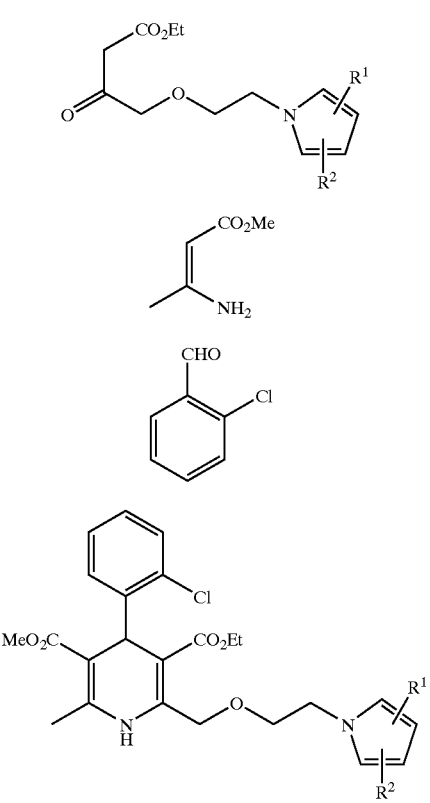

(III)

(IV)

(V)

wherein
R¹ and R² are independently halogen or $C_{1-4}$ alkyl, or $C_{1-4}$ alkyl substituted with hydrogen or alkoxy,
Me is methyl; and
Et is ethyl.

DETAILED DESCRIPTION OF THE INVENTION

The method of the present invention may be represented as Scheme 6, as follows:

Scheme 6

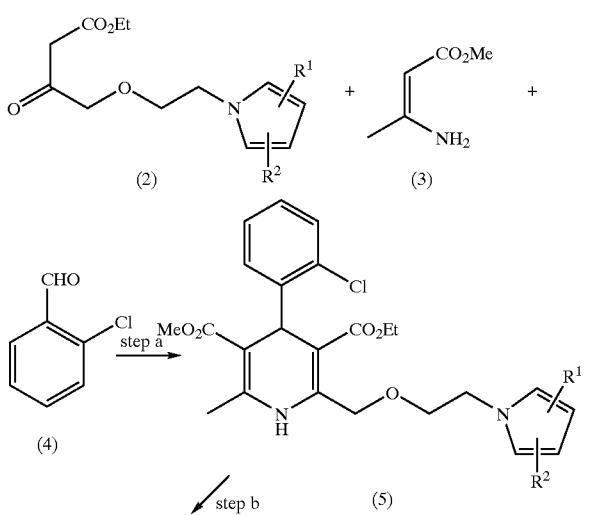

(1)

wherein R¹, R², Et and Me are as defined above.

The pyrrole derivative of formula (II) is a novel compound, and in practicing the present invention, both R¹ and R² are preferably methyl. The pyrrole derivative of formula (II) may be prepared in a high yield in accordance with the method disclosed in [*J. Chem. Soc.,* Perkin Trans. I, 2801, (1984)], which is presented herein as Scheme 7, wherein the amine residue is protected in the form of pyrrole.

Scheme 7

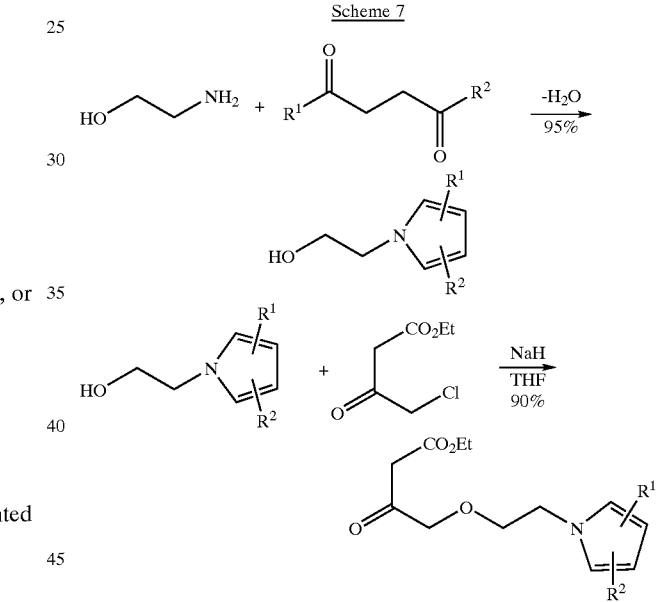

(2)

wherein R¹, R² and Et are as defined above.

The inventive method is particularly advantageous in that the pyrrole group makes it possible to carry out the substitution reaction even under a strong basic condition, in a high yield, i.e., 90%. Such a basic condition is not practicable when any of the conventional amine protecting groups is employed. Also, the pyrrole group can be easily converted into an amine by the action of hydroxylamine without affecting the adjacent ester-protecting group.

In step (a) of the inventive method, a high yield of a compound of formula (V) can be obtained by performing a Hantzsch reaction of a pyrrole derivative of formula (II) with methyl aminocrotonate of formula (III) and 2-chlorobenzaldehyde, the reaction being typically carried out by refluxing the pyrrole derivative, aminocrotonate and 2-chlorobenzaldehyde in 0.9–1.2:1:1 equivalent amounts in an organic solvent for twenty (20) hours. The organic solvent may be a $C_{1-4}$ alkanol such as isopropanol and 1-butanol. The yield of this reaction is about 53% which is much higher than that of a conventional Hantzsch reaction.

In step (b), amlodipine can be obtained in a high yield by refluxing the compound of formula (V) in a mixture of water and an organic solvent for a period ranging from 4 to 5 hours in the presence of a hydroxylamine salt, preferably hydroxylamine hydrochloride, in an amount ranging from 15 to 25 equivalents, preferably 20 equivalents based on the amount of the compound of formula (V). A particularly high yield can be obtained when hydroxylamine hydrochloride is used in combination with triethylamine added in an amount of, e.g., 10 equivalents based on the amount of 1,4-dihydropyridine derivative. The organic solvent may be isopropanol, methanol, ethanol or 1-butanol, and it may be mixed with water in a volume ranging from 3 to 5, preferably 4 based on the volume of water.

In accordance with the present invention, the 1,4-dihydropyridine derivative of formula (V) can be obtained and converted into amlodipine in a much higher yield than was previously possible. This inventive method can thus be advantageously used in mass production of amlodipine.

The present invention is further described in the following Examples which are given for the purpose of illustration only, and are not intended to limit the scope of the invention.

Preparation Example 1

Preparation of 2-(2.5-dimethylpyrrole-1-yl)ethanol 30.5 g (0.5 mol) of aminoethanol, 57 g (0.5 mol) of acetonylaceton and 0.35 g (5 mmol, a catalytic amount) of acetic acid were added to 300 ml of toluene, and then, the mixture was refluxed for 3 hours using a Dean-stark trap. The reaction mixture was cooled to room temperature, 200 ml of water and 100 ml of ethyl acetate were added thereto, and was stirred for 30 minutes. The organic phase was separated and filtered through a silica gel pad, and the filtrate was distilled under a reduced pressure to obtain 66 g of the titled compound in the form of a pale orange oil (yield: 95%).

$^1$H-NMR(300 MHz, CDCl$_3$) δ (ppm): 5.82(s, 2H), 3.94(t, 2H, J=6 Hz), 3.78(t, 2H, J=6 Hz), 2.28(s, 6H)

Preparation Example 2

Preparation of ethyl 4-[2-(2,5-dimethylpyrrole-1-yl)ethoxy]acetoacetate 32 g of sodiumhydride (60% oil dispersion) was added to 500 ml of tetrahydrofuran, and 56 g (0.4 mol) of 2-(2,5-dimethylpyrrole-1-yl)ethanol obtained in Preparation Example 1 was added thereto, followed by stirring at room temperature for 1 hour. The reaction mixture was cooled to 0° C., and a solution obtained by dissolving 65.84 g (0.4 mol) of ethyl 4-chloroacetoacetate in 200 ml of tetrahydrofuran was added thereto dropwise over 2 hours. The mixture was stirred at room temperature for 16 hours and then adjusted to pH 6 to 7 with 3N hydrochloric acid. A sufficient amount of water was added to dissolve solid precipitates formed, and the reaction mixture was extracted two times with 600 ml and 100 ml of ethyl acetate, respectively. Combined ethyl acetate extract was dried over anhydrous magnesium sulfate, treated with decolorizing carbon, and then, the solvent was distilled off under a reduced pressure, to obtain 96.2 g of the titled compound as a pale yellow oil (yield: 90%).

$^1$H-NMR(300 MHz, CDCl$_3$) δ (ppm): 5.86(s, 2H), 4.19(q, 2H, J=7.1 Hz), 4.04(s, 2H), 3.98(t, 2H, J=6.0 Hz), 3.65(t, 2H, J=6.0 Hz), 3.41(s, 2H), 2.23(s, 6H), 1.27(t, 3H, J=7.1 Hz)

Example 1

Preparation of 3-ethyl-5-methyl-2-(2-aminoethoxy-methyl)-4-(2-chlorophenyl)-6-methyl-1,4-dihydro-3, 5-pyridine dicarboxylate (Step a) Preparation of 3-ethyl-5-methyl-2-[(2-(2,5-dimethylpyrrole-1-yl)ethoxy)-methyl]-4-(2-chlorophenyl)-6-methyl-1,4-dihydro-3,5-pyridine dicarboxylate 11.4 g (42.6 mmol) of ethyl 4-[2-(2,5-dimethylpyrrole-1-yl)ethoxy]acetoacetate obtained in Preparation Example 2, 6 g (42.6 mmol) of 2-chlorobenzaldehyde and 4.9 g (42.6 mmol) of methyl 3-aminocrotonate were added to 100 ml of isopropanol, and the mixture was refluxed for 20 hours. The reaction mixture was cooled to room temperature and was concentrated by removing the solvent under a reduced pressure. The residue was purified through column chromatography to obtain 11 g of the titled compound (a light yellow crystal, yield: 53%).

m.p.: 46–48° C.

Mass: m/z=509:11(M+Na)$^+$, 485.94(M+H)$^+$ $^1$H-NMR(300 MHz, CDCl$_3$) δ (ppm): 7.07~7.36(m, 4H), 6.65(b, 1H, NH), 5.86(s, 2H), 5.40(s, 1H), 4.73(s, 2H), 4.03~4.11(m, 4H), 3.74(t, 2H, J=5.4 Hz), 3.64(s, 3H), 2.31 (s, 6H), 2.27(s, 3H), 1.24(t, 3H, J=7.1 Hz)

IR(KBr): 3377, 2977, 2945, 1692, 1480, 1433, 1305cm$^{-1}$ (Step b) Preparation of 3-ethyl-5-methyl-2-(2-aminoethoxy-methyl)-4-(2-chlorophenyl)-6-methyl-1,4-dihydro-3,5-pyridine dicarboxylate 7.9 g (16.2 mmol) of 3-ethyl-5-methyl-2-[(2-(2,5-dimethylpyrrole-1-yl)ethoxy)-methyl]-4-(2-chlorophenyl)-6-methyl-1,4-dihydro-3,5-pyridine dicarboxylate obtained in step a, 22.6 g (324 mmol, 20 eq) of hydroxylamine hydrochloride and 16.4 g (162 mmol, 10 eq) of triethylamine were added to a mixture of 60 ml of isopropanol and 15 ml of water, and the reaction mixture was refluxed for 4.5 hours. The reaction mixture was cooled to room temperature, and isopropanol was distilled off under a reduced pressure. 100 ml of water was added to the residue and adjusted to pH 1 to 2 with 3N HCl, followed by washing two times with 50 ml portions of ethyl ether. The aqueous phase was adjusted to pH 8 to 9 with 1N NaOH, and then extracted two times with 100 ml portions of ethyl acetate. The organic phase was washed with saturated saline, dried over anhydrous magnesium sulfate, and then, the solvent was distilled off under a reduced pressure. The residue was purified through column chromatography to obtain 5.1 g of the titled compound in the form of light yellow foam (yield: 77%).

$^1$H-NMR(300 MHz, CDCl$_3$) δ (ppm): 7.40(br, s, 1H, NH), 7.02~7.37(n, 4H, ArH), 5.39(s, 1H), 4.75(d.d., 2H), 4.02(q, 2H), 3.71(m, 2H), 3.60(s, 3H), 3.12(m, 2H), 2.70(br, 2H, NH), 2.36(s, 3H), 1.19(t, 3H)

As shown above, the method of the present invention is capable of providing amlodipine in a markedly higher yield than any of the conventional methods.

While the invention has been described with respect to the above specific embodiments, it should be recognized that various modifications and changes may be made to the invention by those skilled in the art which also fall within the scope of the invention as defined by the appended claim.

What is claimed is:

1. A method of preparing amlodipine of formula (I) which comprises:

(a) performing a Hantzsch reaction of a compound of formula (II) with aminocrotonate of formula (III) and 2-chlorobenzaldehyde of formula (IV) to obtain a compound of formula (V); and (b) treating the compound of formula (V) with hydroxylamine hydrochloride in a mixture of water and an organic solvent

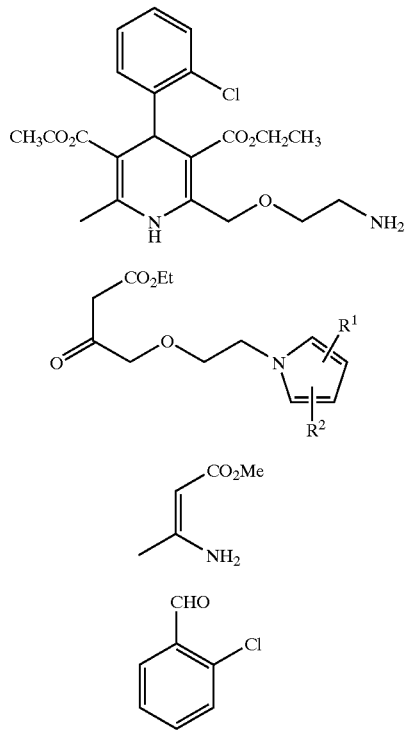

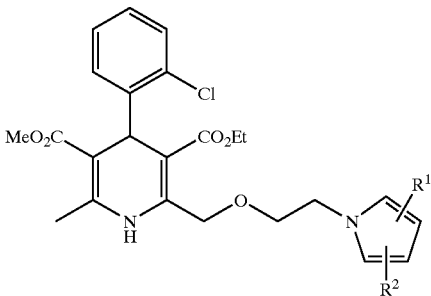

wherein $R^1$ and $R^2$ are independently hydrogen, $C_{1-4}$ alkyl, or $C_{14}$ alkyl substituted with halogen or alkoxy, Me is methyl, and Et is ethyl.

2. The method of claim 1, wherein step (a) is performed by refluxing a 0.9–1.2:1:1 molar mixture of the compound of formula (II), aminocrotonate and 2-chlorobenzaldehyde in an organic solvent.

3. The method of claim 1, wherein step (b) is performed by refluxing the compound of formula (V) in the presence of hydroxylamine hydrochloride in an amount ranging from 15 to 25 equivalents based on the amount of the compound of formula (V).

4. The method of claim 1, wherein step (b) is conducted in the presence of triethylamine employed in an amount of 10 equivalents based on the amount of the compound of formula (V).

5. The method of claim 2, wherein $R^1$ and $R^2$ are methyl.

* * * * *